US005674986A

United States Patent [19]

Viski et al.

[11] Patent Number: 5,674,986

[45] Date of Patent: Oct. 7, 1997

[54] PHOTOGRAPHICALLY USEFUL COMPOUNDS INCLUDING AT LEAST ONE 1,3-SULFUR-OXYGEN RING SYSTEM

[75] Inventors: Peter Viski; David P. Waller, both of Lexington, Mass.

[73] Assignee: Polaroid Corporation, Cambridge, Mass.

[21] Appl. No.: 645,258

[22] Filed: May 13, 1996

Related U.S. Application Data

[62] Division of Ser. No. 556,534, Nov. 13, 1995, Pat. No. 5,569,574.

[51] Int. Cl.[6] .......................... C09B 29/01; C09B 29/36; C09B 29/036; C09B 29/15; C07D 233/02

[52] U.S. Cl. ...................... 534/648; 534/573 L; 534/649; 534/751; 534/797; 534/799; 540/74; 540/874; 548/311.1

[58] Field of Search .................................... 534/648, 649, 534/751, 797, 799, 573 L; 549/74, 874

[56] References Cited

U.S. PATENT DOCUMENTS

| | | | |
|---|---|---|---|
| 3,719,489 | 3/1973 | Cieciuch et al. | 96/29 D |
| 4,098,783 | 7/1978 | Cieciuch et al. | 260/147 |
| 5,021,329 | 6/1991 | Kawagishi et al. | 430/543 |
| 5,328,799 | 7/1994 | Freedman et al. | 430/200 |
| 5,415,970 | 5/1995 | Arnost et al. | 430/200 |

FOREIGN PATENT DOCUMENTS

| | | | |
|---|---|---|---|
| 59-180548 | 10/1984 | Japan | 430/200 |

*Primary Examiner*—Floyd D. Higel
*Attorney, Agent, or Firm*—Jennifer A. Kispert

[57] ABSTRACT

There are described heat-developable photosensitive image-recording materials which include a compound having at least one cyclic 1,3-sulfur-oxygen moiety. The compound is stable in the photographic processing composition but capable of undergoing cleavage in the presence of an image-wise distribution of silver ions and/or soluble silver complex made available as a function of development to liberate a reagent in an imagewise distribution corresponding to that of the silver ion and/or the soluble silver complex. The reagent includes a photographically useful group such as a complete dye or dye intermediate.

20 Claims, No Drawings

PHOTOGRAPHICALLY USEFUL COMPOUNDS INCLUDING AT LEAST ONE 1,3-SULFUR-OXYGEN RING SYSTEM

This is a division of application Ser. No. 08/556,534, filed Nov. 13, 1995 now U.S. Pat. No. 5,569,574.

BACKGROUND OF THE INVENTION

The present invention relates to image-recording materials and, more particularly, to compounds which are stable in the photographic processing composition but capable of undergoing cleavage in the presence of an imagewise distribution of silver ions and/or a soluble silver complex containing silver ions made available as a function of development to liberate a reagent in an imagewise distribution corresponding to that of said silver ion and/or said complex. In one embodiment, the compound is substantially non-diffusible in the photographic processing composition and the reagent released therefrom as a function of development is diffusible in the processing composition.

It is well known that various cleavage reactions are assisted by silver ions including reactions involving cleavage of a compound into one or more fragments. U.S. Pat. No. 3,719,489 discloses silver ion assisted cleavage reactions useful in photographic systems. As disclosed therein, compounds are capable of undergoing cleavage in the presence of silver ions made available imagewise during processing of a silver halide emulsion to liberate a reagent, such as a photographically active reagent comprising, for example, an aldehyde or a color-providing compound, in an imagewise distribution corresponding to that of said silver ions. It is well known in the art that compounds useful for liberating a reagent include 1,3-sulfur-nitrogen compounds, e.g., thiazolidines, and their vinyl and phenylene analogs.

In one embodiment disclosed in U.S. Pat. No. 3,719,489, color images are produced by using as the compounds, color providing compounds which are substantially non-diffusible in the photographic processing composition but capable of undergoing cleavage in the presence of the imagewise distribution of silver ions and/or soluble silver complex made available in the undeveloped and partially developed areas of a silver halide emulsion as a function of development to liberate a more mobile and diffusible color-providing moiety up in an imagewise distribution corresponding to the imagewise distribution of said ions and/or said complex. The subsequent formation of a color image is the result of the differential in diffusibility between the parent compound and liberated color-providing group whereby the imagewise distribution of the more diffusible color-providing moiety released in the undeveloped and partially developed areas is free to transfer.

Color-providing compounds useful in the above process form the subject matter of U.S. Pat. No. 4,098,783, a continuation in part of said U.S. Pat. No. 3,719,489. The color-providing compounds disclosed therein may include one or more dye radicals and one or more 1,3-sulfur-nitrogen moieties. For example, they may comprise one complete dye or dye intermediate and one cyclic 1,3-sulfur-nitrogen moiety. Alternatively, the color-providing compounds may comprise two or more cyclic moieties for each dye radical or dye intermediate or vice versa.

Heat-developable photosensitive imaging materials are well known in the art, including thermally developable black and white as well as color photosensitive materials. Further, it is known in the art that such imaging materials may include various image dye-providing materials to provide the desired image. For example, Japanese Kokai 59-180548 having a Laid-Open date of Oct. 13, 1984 discloses a heat-developable silver halide photosensitive imaging system wherein the dye-providing material contains a heterocyclic ring containing a nitrogen atom and a sulfur or selenium atom which heterocyclic ring is subject to cleavage in the presence of silver ions to release a diffusible dye. As mentioned above, an example of a suitable dye-providing material is a thiazolidine dye such as disclosed in U.S. Pat. No. 4,098,783. The process involves imagewise exposing the photosensitive system to light and subsequently or simultaneously heating the photosensitive system, in the presence of a base or base precursor, under a substantially water-free condition whereby an oxidation-reduction reaction between the exposed photosensitive silver halide and a reducing agent occurs. In the exposed areas, a negative silver image is formed. In the unexposed areas, the silver ion, present in inverse proportion to the silver image, causes the heterocyclic ring of the dye-providing material to be cleaved, releasing a diffusible dye. The diffusible dye is then transferred to an image-receiving layer, whereby a positive dye image is formed.

However, while the differential in diffusibility between the parent compound and the liberated color-providing moiety, disclosed in U.S. Pat. No. 3,719,489, is useful in obtaining a color image, under some conditions a small amount of the parent compound may also transfer.

One way to lessen the diffusion of uncleaved dye-providing material is to use additional dye providing radicals as ballast groups. Another way to lessen the diffusion of uncleaved dye-providing material is to add additional ballasting groups and/or to increase the size of the ballast groups. U.S. Pat. No. 5,320,929 teaches the decrease in diffusion of particular color-providing compounds by using additional color-providing radicals and/or ballast groups. U.S. Pat. No. 5,415,970 discloses additional dye providing radicals as ballast groups to decrease diffusion of the uncleaved parent compound to the receptive layer of the film unit while increasing the image-forming efficiency of the color-providing materials, i.e., releasing more dye-providing moieties per molecule of uncleaved color-providing material. However, while these techniques do lessen such diffusion of the uncleaved parent compound to the receptive layer of the film unit, the results obtained are not entirely satisfying.

Though certain 1,3-sulfur-oxygen compounds have been used in photographic processes, for example, in color-masking during color formation as described in U.S. Pat. No. 5,021,329, 1,3-sulfur-oxygen compounds have not been used in a photographic system to provide an imagewise distribution of a reagent.

As the state of the art advances, novel approaches continue to be sought in order to attain the required performance criteria for these systems. The present invention relates to novel image-recording materials.

SUMMARY OF THE INVENTION

There is provided according to the invention a heat-developable photosensitive image-recording material which includes a compound having at least one cyclic 1,3-sulfur-oxygen moiety represented by formula (I)

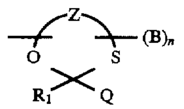

(I)

wherein:

$R^1$ is represented by any of the formulae below (IIa)

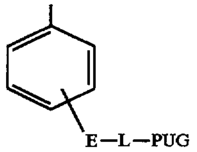

(IIb)

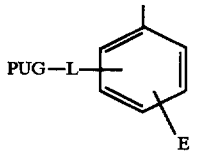

(IIc)

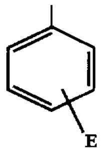

E represents an electron donating substituent, such as amino, substituted amino, alkoxy, hydroxyl, alkyl, aryl, thioalkyl groups; L represents a divalent organic linking group containing at least one carbon atom; PUG represents a photographically useful group such as a dye radical, an antifoggant, a silver solvent, or a development restrainer;

Q represents a hydrogen atom, alkyl, alkoxy, thioalkyl, benzene or electron-rich aryl groups such as dimethylaminobenzene, or Q may be the same as $R_1$ when $R_1$ is represented by formula (IIa) or formula (IIb), or Q may be represented by formula (IIa) or formula (IIb) when $R_1$ is represented by formula (IIb) or formula (IIa), respectively; or when $R_1$ is represented by formula (IIc), Q may be -L-PUG-, provided that at least one of $R_1$ and Q includes PUG;

Z represents the carbon atoms necessary to complete an unsubstituted or substituted 5- or 6-membered heterocyclic ring system; and B represents a ballast group such as an alkyl group having from 10 to 22 carbon atoms or a phenyl ring with an attached alkyl group having from 8 to 22 carbon atoms which renders the compound substantially immobile and nondiffusible in the imaging media, n is an integer from 0 to 4.

The compounds according to the invention may have one or more 1,3-sulfur-oxygen moieties and one or more photographically useful groups. For example, the compounds may have one cyclic 1,3-sulfur-oxygen moiety and one photographically useful group. Compound (i) exemplifies a preferred embodiment wherein the compound has one cyclic 1,3-sulfur-oxygen moiety and one photographically useful group.

As mentioned above, the compounds of the invention may have two or more photographically useful groups for each cyclic 1,3-sulfur-oxygen moiety and vice versa. For example, according to formula (I), when Q is the same as $R_1$, and $R_1$ is represented by either formula (IIa) or (IIb), a cyclic 1,3-sulfur-oxygen moiety may have more than one photographically useful group.

The compounds disclosed herein have from one to four and, preferably, one or two cyclic 1,3-sulfur-oxygen moieties represented by formula (I). The additional moieties may be attached through the carbon atoms represented by Z in formula (I). Additional points of attachment will be described hereinafter in conjunction with the detailed description of several preferred embodiments of the invention. Further, it will be understood that when the compound has only one cyclic 1,3-sulfur-oxygen moiety, the bond line shown in formula (I) represents an attachment of a hydrogen atom to any of the carbon atoms represented by Z.

The compounds of the present invention are useful in photographic imaging systems utilizing silver halide wherein the method of processing employs either wet processing to develop the image such as disclosed in U.S. Pat. Nos. 3,719,489 and 4,740,448, photothermographic or thermographic processing wherein image formation includes a heating step. As mentioned previously, the thermally processed photographic systems may be those processed in the presence or absence of water. In addition, the thermally processed photographic systems may be those processed in the presence or absence of a base or a base-precursor, i.e., a compound which generates a base under the processing conditions, such as those disclosed in U.S. Pat. No. 3,260,598.

According to a particularly preferred embodiment of the invention, the compounds of the present invention are capable of releasing a color providing group in the presence of the imagewise distribution of silver ions or silver salt complex made available during processing of a silver halide emulsion, in an imagewise distribution corresponding to that of the silver ions.

Another use of the color-providing compounds is in thermographic imaging systems where a source of silver ions or a soluble silver complex becomes available, upon heating in an imagewise manner, to cleave the color-providing compound. One of skill in the art will be able to choose from among the color-providing compounds of the invention by choice of substituents, e.g., solubilizing groups such as carboxylic acids, sulfonic acids, and phosphonic acids, so that they will function as desired in a particular system.

These and other objects and advantages which are provided in accordance with the invention will in part be obvious and in part be described hereinafter in conjunction with the detailed description of various preferred embodiments of the invention. The invention accordingly comprises the processes involving the several steps and relation and order of one or more of such steps with respect to each of the others, and the product and compositions possessing the features, properties and relation of elements which are exemplified in the following detailed disclosure, and the scope of the application of which will be indicated in the claims.

DETAILED DESCRIPTION OF THE PREFERRED EMBODIMENTS

The compound of the present invention contains at least one cyclic 1,3-sulfur-oxygen moiety represented by formula (I) having the group —S—C—O— included in the ring. The ring undergoes cleavage between the S atom and the C atom common to the S and O atoms and between the O atom and the common C atom. Cleavage occurs in the presence of the imagewise distribution of silver ions and/or soluble silver complex made available in the undeveloped and partially developed areas of the photosensitive emulsion in an imagewise distribution corresponding to the imagewise distribution of said ions and/or said complex. Upon cleavage of the ring, a more mobile and diffusible reagent is liberated which contains a photographically useful group such as a dye.

A preferred compound according to the invention is represented by formula (III) below:

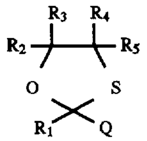

(III)

wherein:

$R_1$ and Q are as described above; and $R_2$, $R_3$, $R_4$, and $R_5$ are each independently hydrogen, a monovalent organic radical such as a phenyl ring, an alkyl group, or a ballast group such as an alkyl chain having from 10 to 22 carbon atoms or a phenyl ring with an attached alkyl group having from 8 to 22 carbon atoms, or a chemical linkage such as a single covalent bond or a multivalent organic group which may join a cyclic 1,3-sulfur-oxygen moiety(ies), or taken together, $R_2$ and $R_3$, $R_3$ and $R_4$, or $R_4$ and $R_5$ represent a substituted or unsubstituted 5- or 6-membered carbocyclic or heterocyclic ring. It is preferred that one of $R_2$ to $R_5$ is a ballast group, particularly in those instances when the compound has only one cyclic 1,3-sulfur-oxygen moiety.

As mentioned earlier, the compounds of the invention may contain one or more cyclic 1,3-sulfur-oxygen moieties. It will be understood that when the compound has only one cyclic 1,3-sulfur-oxygen moiety, the bond line shown in formula (I) represents an attachment of a hydrogen atom to any of the carbon atoms represented by Z. When the compound has more than one cyclic 1,3-sulfur-oxygen moiety, these additional cyclic 1,3-sulfur-oxygen moieties may be attached in various ways such as the cyclic 1,3-sulfur-oxygen moieties being attached to each other through their carbon atoms represented by Z in formula (I). For example, an embodiment wherein the 1,3-sulfur-oxygen moieties are joined to each other through their carbon atoms is shown below:

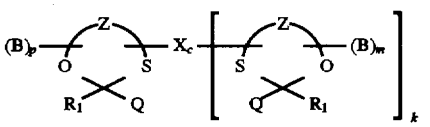

(IV)

wherein:

$R_1$ Q, Z, and B are as described above;

X represents a multivalent chemical linkage;

c is 0 or 1;

p is an integer from 0 to 3;

m is an integer from 0 to 3; and k is 0 when c is 0; and k is 1,2, or 3 when c is 1.

It will be apparent that in this embodiment c is 1. It will also be apparent that when the compound contains only one cyclic 1,3-sulfur-oxygen moiety, c is 0. Furthermore, it will be apparent that one, two, or three cyclic 1,3-sulfur-oxygen moieties may be joined through the multivalent chemical linkage represented by X in formula (IV) above. Where there are two cyclic 1,3-sulfur-oxygen moieties joined together, various orientations are possible in addition to the orientation depicted by formula (IV) above

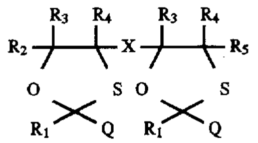

(Va)

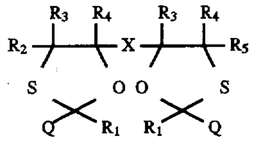

(Vb)

wherein:

$R_1$, $R_2$, $R_3$, $R_4$, $R_5$, X, and Q are as described above. It will be apparent from formulae (IV), (Va), and (Vb) that cyclic 1,3-sulfur-oxygen moieties represented by formula (I) may be joined together in various orientations including —O—S— to —S—O——O—S— to —O—S—, or —S—O— to —O—S—.

The photographically useful group itself may have a substituent. For example, in a preferred embodiment of the invention, the substituent attached to the photographically useful group may be represented by formula (VI) below:

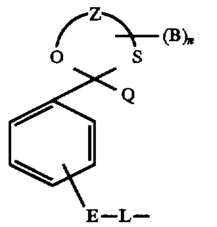

(VI)

wherein:

E, L, Q, Z, B, and n are as described above.

Compound (ii) includes a substituent illustrated by formula (VI).

It will also be apparent from both formula (IV) and formula (I) that the compounds of the invention may have more than one photographically useful group. For example, according to formula (I), when Q is the same as $R_1$, and $R_1$ is represented by either formula (IIa) or (IIb), a cyclic 1,3-sulfur-oxygen moiety may have more than one photographically useful group.

In a preferred embodiment, color images are produced by using as the compounds, color-providing compounds which include color-providing group(s). The term color-providing group is used herein to mean a complete dye or dye intermediate capable of yielding a complete dye upon subsequent reaction. The term "complete dye" is used herein to mean a dye radical having the chromophoric system of a dye.

As suggested above, the photographically useful group, PUG, according to the invention, may be a color-providing group, e.g., a complete dye or dye intermediate capable of yielding a complete dye upon subsequent reaction, for example, upon reaction with a suitable coupler to form a complete dye. The coupling reaction may take place directly after cleavage of the cyclic 1,3-sulfur-oxygen moiety to liberate the dye intermediate, or it may take place after diffusion of the dye intermediate to, e.g., an image-receiving layer.

Complete dyes which may be used in the present invention include any of the general classes of dyes heretofore known in the art, for example, nitro, thiazole, cyanine, di- and triphenylmethane, anthrapyridone, azo, anthraquinone, phthalocyanine and metal complexed azo, azomethine and phthalocyanine dyes. Specific radicals of organic dyes that may be used include the dye radicals comprising the dye portion of the dye developers disclosed in U.S. Pat. Nos. 3,076,808; 3,076,820; 3,134,762; 3,134,763; 3,134,764; 3,134,765; 3,135,734; 3,173,906; 3,186,982; 3,201,384; 3,208,991; 3,209,016; 3,218,312; 3,236,864; 3,236,865; 3,246,016; 3,252,969; 3,253,001; 3,255,206; 3,262,924; 3,275,617; 3,282,913; 3,288,778; 3,299,041; 3,303,183; 3,306,891; 3,337,524; 3,337,589; 3,357,969; 3,365,441; 3,424,742; 3,482,972; 3,491,127; 3,544,545; 3,551,406; 3,597,200; 3,752,836; 4,264,701; and 4,267,251.

The dye intermediates which may be used in the present invention may be any molecule which when released is capable of forming a dye upon reaction with another molecule. For example, see U.S. Pat. No. 3,719,488 which discloses the use of 1,3-sulfur-nitrogen compounds to provide the imagewise distribution of dye intermediate an/or color-forming reagent, e.g., a colorless aldehyde or ketone dye intermediate which, when released is capable of reacting with a color-forming reagent, such as a methylene coupler, to form a complete dye.

In addition to the above, useful color-providing groups to be used in an embodiment of the present invention wherein the photographically useful group is a dye include compounds which are colorless or of a color other than that ultimately desired in a certain environment, such as at a particular pH level, but upon a change in the environment, e.g., from acid to alkaline conditions, undergo a color change. Color-providing materials of this nature include indicator dyes and leuco dyes. It is also contemplated that dyes may be employed which undergo a color shift or change in spectral absorption characteristics during or after processing. Such dyes may be referred to as 'temporarily shifted' dyes. The temporary shift may, for example, be effected by acylation, the acyl group being removable by hydrolysis in an alkaline environment, see for example, U.S. Pat. No. 4,535,051. The temporary shift may be effected by an amide group which undergoes an intramolecular cleavage to form a colored image dye such as disclosed in U.S. Pat. No. 4,468,451; or the temporary shift may be effected such that the colorless precursor undergoes a β-elimination reaction following the imagewise cleavage of the cyclic 1,3-sulfur-oxygen group to form an image-dye; or the colorless precursor undergoes a β-elimination reaction which generates a moiety capable of undergoing an intramolecular accelerated nucleophilic displacement reaction to provide an image dye as described in U.S. Pat. No. 4,468,450. It is also within the scope of the present invention to employ metal complexed or metal complexable dyes and to employ dyes, the non-complexed forms of which are substantially colorless, but which, when complexed during or subsequent to image formation, are of the desired color.

The choice of color-providing group is primarily limited by the spectral characteristics it is desired to have in the dye product, e.g., oxo-derivative containing the photographically useful group, which is released upon the cleavage of the color-providing compound in the presence of silver ions and/or soluble silver complex.

The linking group, L, may be attached to the cyclic 1,3-sulfur-oxygen moiety as shown in formulae (IIa), (IIb), and, when $R_1$ is represented by (IIc), L is attached to PUG represented by Q in formula (I). L may be any divalent organic radical possessing at least one carbon atom for attachment to the cyclic 1,3-sulfur-oxygen moiety either by a single covalent bond or by a spiro union.

Linking groups are well known in the photographic art, and as discussed in U.S. Pat. Nos. 2,983,606 and 3,255,001, they are used to unite a dye radical of a desired predetermined color with a group possessing a silver halide developing function to obtain a dye developer. Ordinarily, the linking group functions as an insulating linkage to prevent or interrupt any system of conjugation or resonance extending from the dye radical comprising the chromophoric system of a dye to the developer group. The linking groups used in the dye developer art, either insulating or non-insulating, are also useful in the embodiment wherein the photographically useful group is a dye for uniting the dye radical with the cyclic 1,3-sulfur-oxygen moiety.

Preferably, the linking groups used in the compounds of the invention to connect PUG to the cyclic 1,3-sulfur-oxygen moiety are divalent hydrocarbon residues, e.g., alkylene groups, e.g., $(—CH_2—)_3$, $(CH2—)_4$, cycloalkylene groups, aralkylene groups, e.g., $—CH_2—Ar—$ wherein Ar represents arylene and alkarylene groups, e.g., $—CH_2—Ph—CH_2—$ where Ph represents a substituted or unsubstituted phenyl ting, or —CONH—; alkylene-CONH—; and arylene-CONH—.

As mentioned above, PUG represents a photographically useful group. PUG may be attached to the cyclic 1,3-sulfur-oxygen moiety as shown in formulae (IIa), (IIb), and, when $R_1$ is represented by (IIc), as attached to L represented by Q in formula (I). Examples of PUGs include antifoggants, antistatic agents, auxiliary developing agents, bleach accelerators, bleach inhibitors, chelating agents, chemical sensitizers or desensitizers, competing couplers, competitive compounds, contrast improvers, couplers, coupler-releasing couplers, crosslinking groups, desilvering accelerators, desilvering inhibitors, desensitizers, developing agents, development accelerators, development inhibitors, development restrainers, diffusive dyes, DIR hydroquinones and precursors thereof, dot improvers, dyes, dye image stabilizers, dye precursors, electron transfer agents, film hardeners, fixing accelerators, fixing inhibitors, fluorescent brightening agents, fogging agents, fog inhibitors, hardeners, image dye-forming couplers, image stabilizers, image toners, mordant groups, mordant polymers, nondiffusive dyes, nucleation accelerators, nucleators, optical brighteners, photographically useful polymers or precursors thereof, photographic dyes, post-processing image stabilizers, pre-processing image stabilizers, processing dependency improvers, reducing agents, silver halide complexing agents, silver halide solvents, silver ion fixing agents, spectral sensitizers or desensitizers, surface active agents, surfactants, tanning agents, toners, and ultraviolet radiation absorbents.

Z in formula (I), as stated above, represents the atoms necessary to complete either a substituted or unsubstituted 5- or 6-membered heterocyclic ring. Preferably, the heterocyclic ring is a 5-membered oxathiolane ring represented by formula (VII)

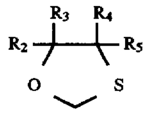

(VII)

wherein:

$R_2$, $R_3$, $R_4$ and $R_5$ are as described in formula (III). Formula (VII) also includes the corresponding substituted oxathiolanes. As mentioned previously, one of skill in the art will be able to choose from among the compounds of the invention by choice of substituents, e.g., solubilizing groups such as those described in U.S.

Pat. No. 4,886,744, so that they will function as desired in a particular system.

A function of the ballast group(s), B, is to render the compounds of the invention substantially immobile and nondiffusible in the imaging media during processing. Many ballast groups are known in the art. The ballast group(s) may be anything which lessens the diffusion of uncleaved parent compound, such as disclosed in U.S. Pat. No. 5,340,689.

The selection of a particular ballast group, if any, will depend on a number of factors, e.g., on the particular imaging system in which the compounds are to be used and whether it is desired to employ only one ballast group or to employ more than one group capable of insolubilizing or immobilizing the compound. Where more than one group is employed to render the compound substantially non-diffusible, lower alkyl radicals may be used. Where only one group is utilized for ballasting, it is more effective to employ, for example, a higher alkyl radical, such as decyl, dodecyl, lauryl, stearyl, and oleyl; —N—(alkyl)2; or a carbocyclic or heterocyclic ring having 6 members. Where cyclic ballast groups are used, the carbocyclic or heterocyclic ballast group may be bonded to a single atom or to adjacent atoms of the parent molecule and may be bonded to a single atom by a valence bond or through a spiro union.

Any suitable polymeric residue may also be used as a ballast. In a preferred embodiment the ballast is a polymeric residue represented by formula

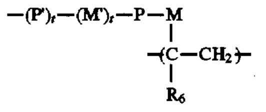

(VIII)

wherein:

$R_6$ represents hydrogen or lower alkyl containing 1 to 6 carbon atoms;

M and M', the same or different, each represent a divalent linking group selected from the group consisting of $-CONH-$, $-NHCO-$, $-C-O-$, $O-C-$, $-SO_2NH-$, and

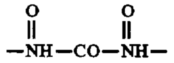

P and P', the same or different, each represent a divalent hydrocarbon group containing at least two carbon atoms; and t is 0 or 1. Compound (xiv) exemplifies a preferred embodiment wherein the ballast group is a polymeric residue.

Generally, the ballasted compounds of the invention are prepared by the reaction of an aldehyde with an α-hydroxy-thiol. Different solvents may be used, e.g., alcohols, esters, aromatic solvents; however, the preferred solvent forms an azeotrope with water. The α-hydroxy-thiols may be synthesized by various methods including the ring opening of an epoxide with SH or the substitution of the halogen in an epihalohydrin.

As previously described, the image-recording materials of the invention may include more than one cyclic 1,3-sulfur-oxygen moiety represented by formula (I). Besides undergoing cleavage in the presence of an imagewise distribution of silver ions and/or soluble silver complex, these additional cyclic 1,3-sulfur-oxygen moieties may decrease diffusion of the uncleaved parent compound to the receptive layer of the film unit while increasing the image-forming efficiency of the reagents, for example, by releasing more dye-providing moieties per molecule of uncleaved color-providing material.

The chemical linkage, depicted as X in the preferred embodiment shown in formula (IV), may be a single covalent bond, as where the atoms of the respective cyclic 1,3-sulfur-oxygen moieties are directly joined to each other by a shared pair of electrons, e.g., through any of their respective carbon atoms except the carbon atom common to both the O and S atoms. Alternatively, the groups may be joined using a multivalent organic group, i.e., an organic group having two, three or four free valences attached to different atoms and joined to each of the respective atoms of the cyclic 1,3-sulfur-oxygen moieties by a single covalent bond. U.S. Pat. No. 5,415,970 discloses that, preferably, the chemical linkage is a multivalent organic group and, provides examples of suitable chemical linkages, X, which may be used in the present invention.

The compounds of the present invention can be prepared using reactions which are known in the art and these will be apparent particularly in view of the specific examples provided herein. Illustrative examples of the compounds according to the invention are represented by the formulae below:

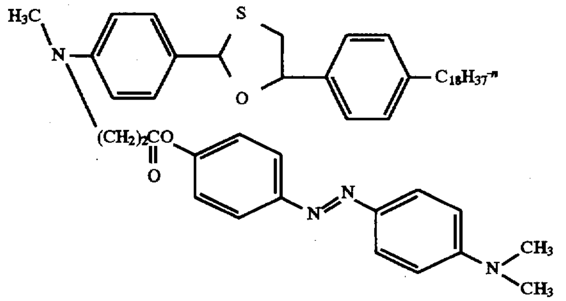

(i)

-continued
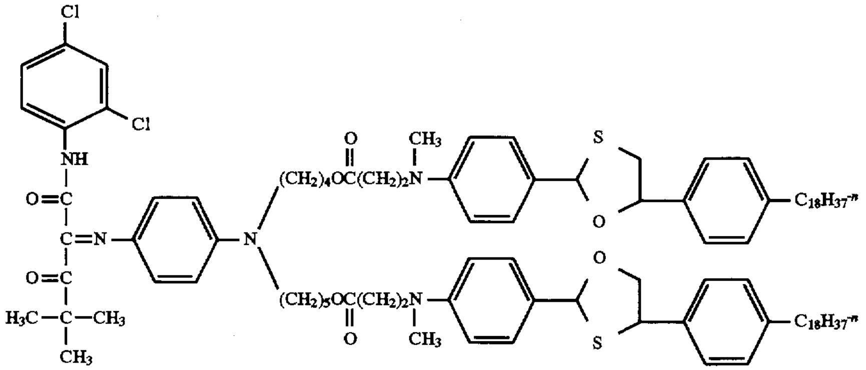
(ii)
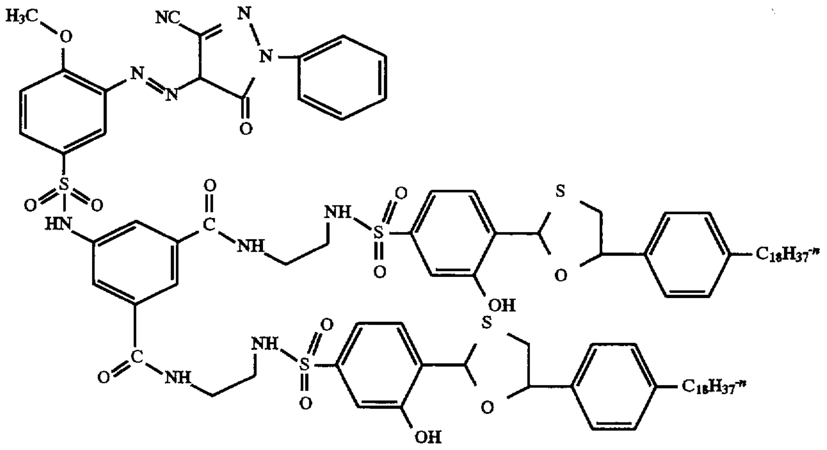
(iii)
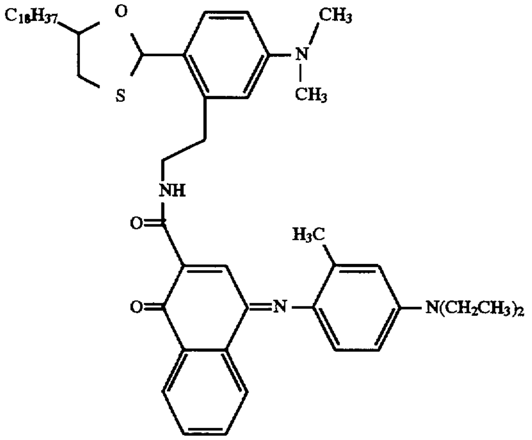
(iv)
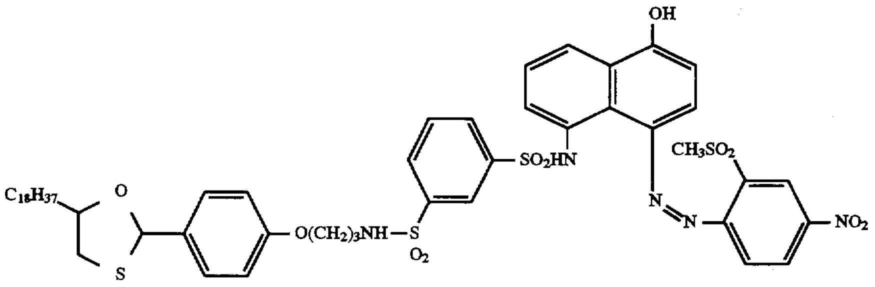
(v)

-continued
(vi)
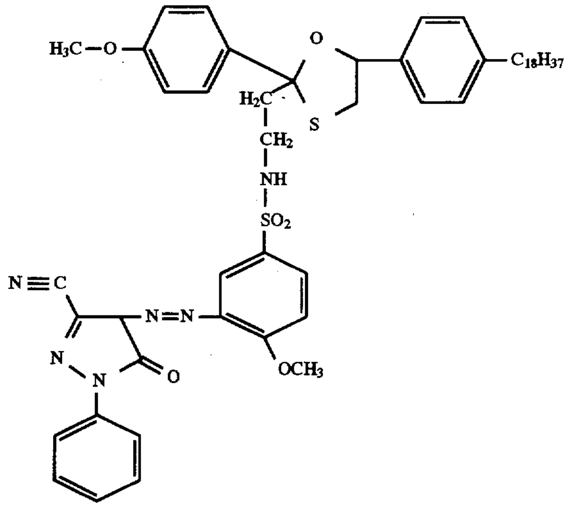
(vii)
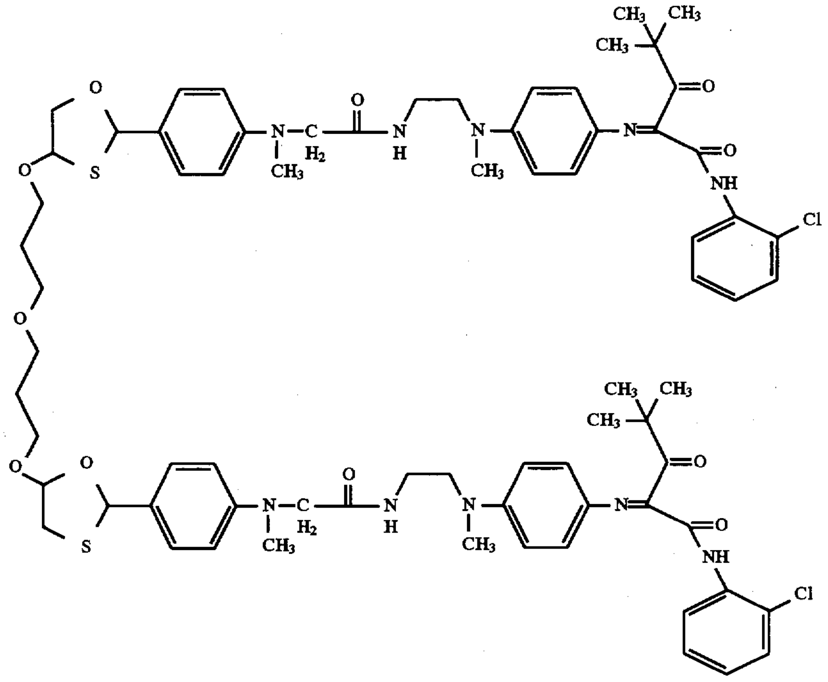
(viii)
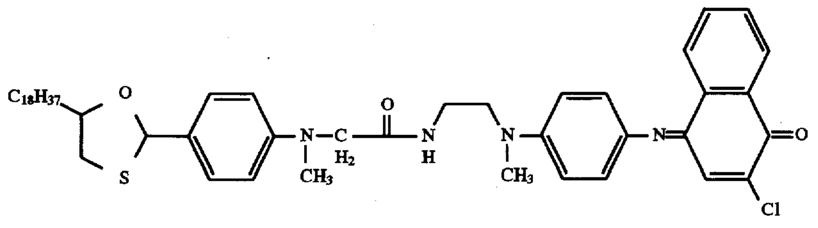
(ix)
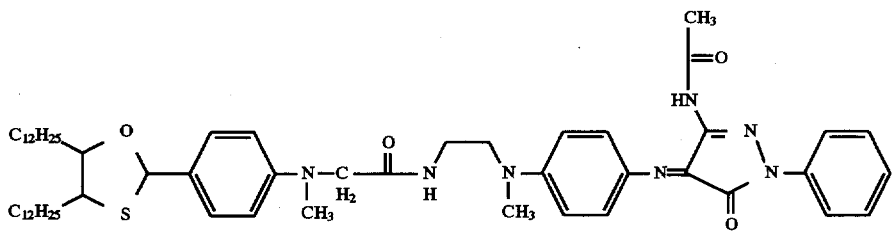

-continued
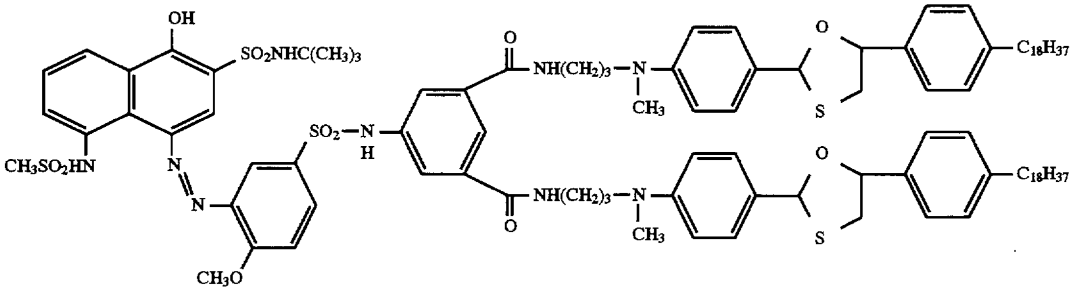
(x)
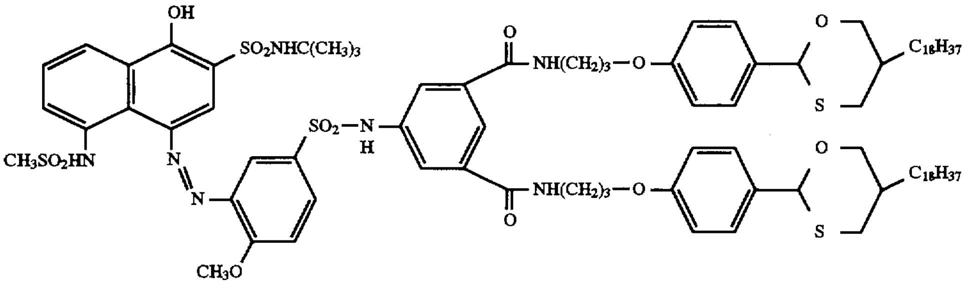
(xi)
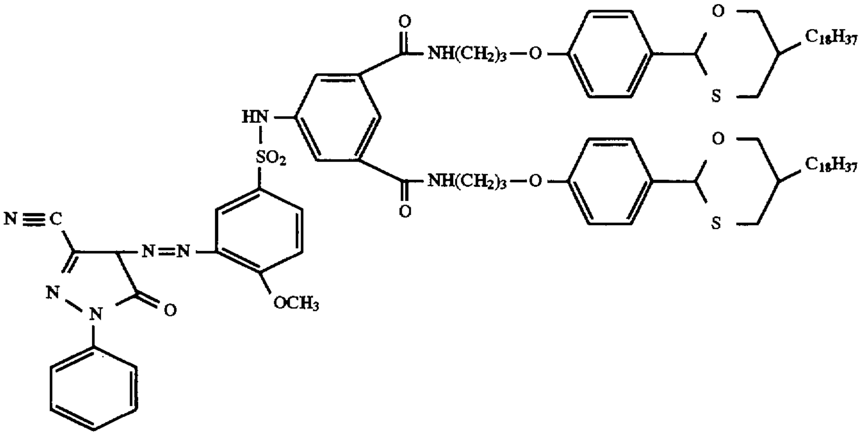
(xii)
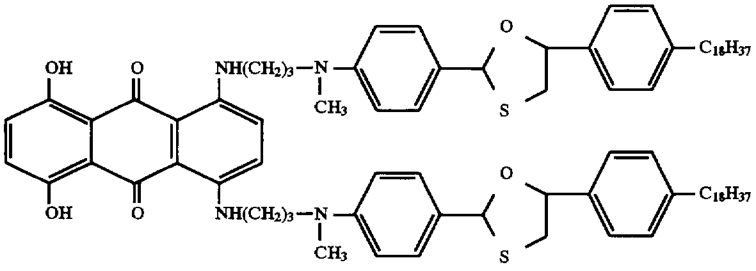
(xiii)

-continued (xiv)

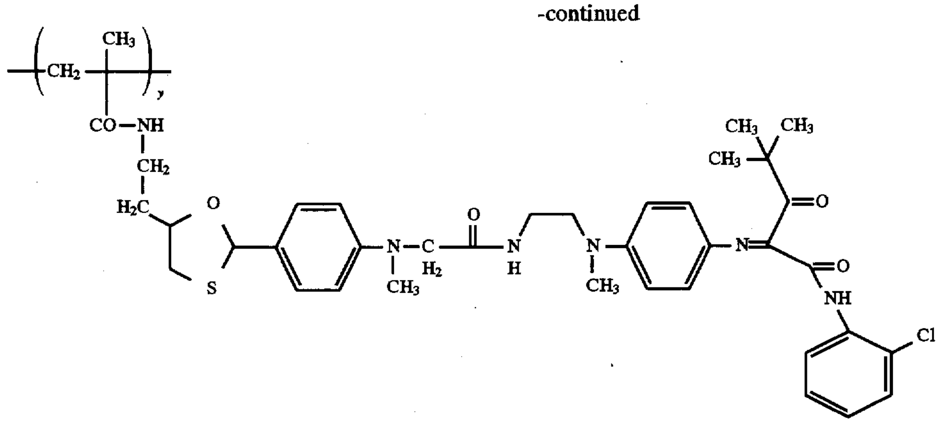

wherein: y is an integer from 10 to 100.

The image-recording materials of the present invention are useful in photographic imaging systems including any of the known diffusion transfer color photographic processes such as thermographic and photothermographic and, therefore, extensive discussion of such elements is not necessary. Briefly, such image recording materials include at least one support carrying in at least one layer: (1) a source of silver ions; (2) a photosensitive silver halide which can also function as the silver ion source; (3) a reducing agent; (4) a compound having at least one cyclic 1,3-sulfur-oxygen moiety represented by formula (I), and (5) an image-receiving layer; however, the image receiving layer may be on a separate support. A preferred photothermographic diffusion transfer image-recording material will now be described in detail.

Accordingly, the support(s) for the image-recording materials must necessarily be able to withstand the heat required for processing the image. The support can be transparent or opaque. Any suitable support can be employed such as those described in Research Disclosure No. 17029, issued June 1978. Specific examples of suitable supports include synthetic polymeric films, such as polyethylene terephthalate, polycarbonate, polyvinyl chloride, polystyrene, polyethylene, polypropylene and polyimide. The above described supports can be made opaque by incorporating pigments therein such as titanium dioxide and calcium carbonate. Other supports include paper supports, such as photographic raw paper, printing paper, baryta paper and resin-coated paper having paper laminated with pigmented thermoplastic resins, fabrics, glass and metals. Preferably, a polyester film is used.

A subcoat may be added to the face of the support which carries the heat-developable photosensitive materials in order to increase adhesion. For example, a polyester base coated with a gelatin subcoat has been found to enhance adhesion of aqueous based layers.

The source of silver ions may be any of those materials commonly employed in the photographic art to provide silver ions provided the silver ion is made available imagewise upon processing to cleave the cyclic 1,3-sulfur-oxygen moiety(ies) of the compound and release the diffusible reagent. Useful materials include silver halides and any of the silver salt oxidizing materials known in the art, such as those described in Research Disclosure No. 17029. Preferably, the photosensitive image-recording material additionally contains a silver salt oxidizing material in a layer other than the image-receiving layer and a reducing agent for silver. For thermographic applications, the silver salt complexes disclosed in U.S. Pat. No. 5,436,108 are particularly useful.

The photosensitive silver halide used in the photothermographic image-recording materials of the present invention may be any photosensitive silver halide employed in the photographic art, such as, silver chloride, iodide, bromide, iodobromide, chlorobromide, etc., and it may be prepared in situ or ex situ by any known method including using a light-sensitive silver halide-forming component in the presence of the silver salt oxidizing material so as to form the light sensitive silver halide in part of the silver salt oxidizer.

The photosensitive silver halide emulsions are typically aqueous silver halide emulsions, and any conventional silver halide precipitation methods may be employed in the preparation of the emulsions. The silver halide emulsions may be spectrally sensitized by any suitable spectral sensitization method in order to extend the photographic sensitivity to wavelengths other than those absorbed by the unsensitized silver halide. Examples of suitable sensitizing materials include cyanine dyes, merocyanine, styryl dyes, hemicyanine dyes and oxonole dyes. In addition to spectral sensitization, the silver halide emulsions may be chemically sensitized using any suitable chemical sensitization technique. Many chemical sensitization methods are known in the art. The silver halide emulsion is generally added to each photosensitive layer in an amount calculated to give a coated coverage in the range of 0.5 to 8.0 mmol/m$^2$, preferably 0.5 to 4.0 mmol/m$^2$.

The silver salt oxidizing material should be relatively light stable and thermally stable under the processing conditions. The silver salt oxidizing material is generally an organic silver salt or silver salt complex as is known in the art. Any organic compound known in the photographic art to be useful for forming the organic silver salt may be employed. See, e.g., the organic silver salts described in U.S. Pat. No. 4,729,942. See U.S. Pat. Nos. 4,260,677 and 5,320,929 for useful silver salt complexes.

Examples of suitable silver salt oxidizing materials include silver salts of carboxylic acids, e.g., behenic and stearic acids and silver salts of compounds having an imino group. Preferred silver salts are the organic silver salts having an imino group. The silver salts of benzotriazole and its derivatives have been found to give particularly good results in the heat-developable photosensitive systems of the present invention.

The silver salt oxidizer used in the present invention can be prepared in a suitable binder by any known means and then used immediately without being isolated. Alternatively, the silver salt oxidizer may be isolated and then dispersed in a suitable binder. The silver salt oxidizer is generally used in an amount ranging from 0.5 to 12.0 mmol/m$^2$, and preferably from 0.5 to 4.0 mmol/m$^2$.

Any suitable reducing agents may be used in the photothermographic image-recording material of the present invention, and these may be selected from among those commonly used in heat-developable photographic materials. Illustrative reducing agents useful in the present invention include hydroquinone and its derivatives, e.g., 2-chlorohydroquinone; aminophenol derivatives, e.g., 4-amino-phenol and 3,5-dibromophenol; catechol and its derivatives, e.g., 3-methoxycatechol; phenylenediamine derivatives, e.g., N,N-diethyl-p-phenylenediamine; and, 3-pyrazolidone derivatives, e.g., 1-phenyl-3-pyrazolidone and 4-hydroxymethyl-4-methyl-1-phenyl-3-pyrazolidone. The preferred reducing agent is 1-phenyl-3-pyrazolidone, commercially available under the tradename Phenidone, and 4-hydroxymethyl-4-methyl-1-phenyl-3- pyrazolidone, commercially available under the tradename Dimezone-S. The reducing agents may be used singly or in combination and they are generally employed in amounts ranging from 0.5 to 10.0 mmol/$m^2$, and preferably 1.0 to 8.0 mmol/$m^2$.

The image-receiving layer may in certain embodiments, e.g., when the photographically useful group is a dye, have the capability of receiving the dye released as a result of thermal development. These image-receiving layers may be prepared by coating a support material with a suitable polymer for receiving the dye. Suitable polymers to be coated on the image-receiving support to receive the dye include polyvinyl chloride, poly(methyl methacrylate), polyester, and polycarbonate. Alternatively, certain polymers may be used as both the support and the dye-receiving material.

The image-receiving layer is generally superposed on the photosensitive element after exposure and the two are then heated simultaneously to develop the image and cause, in this embodiment, the dye to transfer. Alternatively, in another embodiment, the negative may be exposed and then processed with heat, followed by superposing the image-receiving sheet on the exposed and developed photosensitive material and applying heat and pressure to transfer the dye. The image-receiving layer is then generally peeled apart from the negative.

For both the preferred embodiment being discussed in detail, e.g., photothermographic diffusion transfer image-recording material, and thermographic applications, the image-recording material may additionally contain a thermal solvent. Thermal solvents which are useful in heat-developable imaging materials and methods are nonhydrolyzable, thermally-stable compounds which are solids at ambient temperature but which melt at or below the temperature used in thermal processing. The thermal solvent acts as a solvent for various components of the heat-developable photosensitive material, assists in the acceleration of thermal development, and provides the medium for diffusion of various components including silver ions and/or complexes, reducing agents and image dye materials. Many suitable thermal solvents for use in heat-developable photosensitive image recording materials are known in the art. Any suitable thermal solvent may be incorporated in the image-recording materials of the present invention.

Illustrative thermal solvents useful in the present invention include polar organic compounds such as the polyglycols described in U.S. Pat. No. 3,347,675 and the compounds described in U.S. Pat. No. 3,667,959. Particularly useful compounds include urea derivatives, e.g., dimethylurea, diethylurea and phenylurea; amide derivatives, e.g., acetamide, benzamide, m- and p-toluamide; sulfonamide derivatives, e.g., methylsulfonamide, benzenesulfonamide and α-toluenesulfonamide; and polyhydric alcohols, e.g., 1,2-cyclohexanediol and pentaerythritol. Typical suitable thermal solvents, preferably for use with gelatin, and some of their properties, are described in U.S. Pat. No. 5,368,979.

The layers of the image-recording materials of the invention are typically coated from water dispersions, hence, for coatability considerations, it is preferred that the thermal solvents utilized in these image-recording materials have low solubility in water, e.g., less than 1%. In addition, image-recording materials having such thermal solvents typically exhibit enhanced stability during storage.

A single thermal solvent can be incorporated in a layer of the image-recording material or a combination of two or more thermal solvents may be incorporated in a layer. In another embodiment, different thermal solvents may be used separately in different layers of the image-recording elements. In this case, it would be apparent to those skilled in the art that the choice of such thermal solvents should be made such that their use together in the image-recording material would not have any adverse effect upon the image formation process.

Generally, the image-recording materials of an embodiment of the invention utilizing a thermal solvent should have a sufficient amount of thermal solvent to provide a medium for reaction and diffusion which will allow the required imagewise distribution of the reagent to occur. The thermal solvent can be present in one or more layers of the image-recording material. Hence, the thermal solvent may be present in only the photosensitive element, or donor sheet, or only the image-receiving element, or thermal solvent may be present in each of the photosensitive and image-receiving elements. Preferably, the thermal solvent is present in each layer. The total amount of thermal solvent in the image-recording material should be sufficient to dissolve substantially all the binder material which is present. The amount of thermal solvent present in a single layer is typically from 0 to about 10 g/$m^2$ and preferably from about 0.1 to about 1.5 g/m2.

The photosensitive silver halide emulsion layer(s) and other layers of the heat-developable image-recording material may contain various materials as binders. It is known that suitable binders for photosensitive silver halide emulsion layers include water soluble synthetic, high molecular weight compounds such as polyvinyl alcohol and polyvinylpyrrolidone and synthetic or naturally occurring high molecular weight compounds such as gelatin, gelatin derivatives, cellulose derivatives, proteins, starches and gum arabic. A single binder or mixture of binders may be used. A preferred binder material is gelatin.

The layers of the heat-developable photosensitive system according to the present invention which contain a crosslinkable colloid as a binder, e.g., gelatin, can be hardened by using various organic and inorganic hardeners such as those described in T. H. James, *The Theory of the Photographic Process,* 4th Ed., MacMillan, 1977, pp. 77–87. The hardeners can be used alone or in combination. It is preferred that the image-recording materials according to the present invention contain a hardener in the photosensitive silver halide emulsion layer. Any suitable hardener known in the photographic art may be used; however, aldehyde hardeners, e.g. succinaldehyde and glyoxal, have been found to be particularly useful when gelatin is employed as the binder. The hardeners are generally used in amounts ranging from 1 to 10% by weight of the total amount of gelatin coated.

In addition, the heat-developable photosensitive image-recording material also preferably includes an auxiliary ligand for silver. The use of auxiliary ligands in heat-developable photosensitive image-recording materials forms the subject matter of U.S. Pat. No. 5,328,799. Auxiliary ligands for silver which can be used in embodiments of the present invention include 2,2'-bipyrimidine; 1,2,4-triazole and derivatives thereof, e.g., 3-phenyl-5-thienyl-1,2,4-triazole; phosphines, e.g., triphenylphosphine; acyclic thioureas, e.g., N,N'-di-n-butylthiourea and tetramethylthiourea; 3,6-dithia-1,8-octanediol; 6-substituted purines wherein the 6-position is substituted with —OR or —NHR' where R is hydrogen, alkyl, or aryl and R' is alkyl, e.g., 6-methoxypurine and 6-dodecylaminopurine; and, bidentate nitrogenous ligands having two nitrogen atoms which are both available to coordinate to the same silver atom, e.g., 4-azabenzimidazole and derivatives thereof, 2,2'-dipyridyls including 2,2'-dipyridyl, 4,4'-dimethyl-2,2'-dipyridyl and 4,4'-diphenyl-2,2'-dipyridyl and 1,10-phenanthrolines including 1,10-phenanthroline, 5-chloro-1,10-phenanthroline and 5-nitro-1,10-phenanthroline.

When employed, the auxiliary ligand may be present in any layer of the heat-developable photosensitive or thermosensitive system of the present invention including the image-receiving layer. If present in a layer on the image-receiving layer, the layer also preferably contains a thermal solvent in which the ligand is soluble. Alternatively, water soluble ligands may be coated on the negative, e.g., on the layer comprising the photosensitive silver halide, before or after hardening of the gel has been accomplished. If the silver assisted cleavage of the particular compound, e.g., color-providing compound, tends to be slow, it is preferred that the auxiliary ligand be present in a layer other than the image-receiving layer. The auxiliary ligands are generally used in amounts which yield, after drying, a coating coverage of 1 to 36 $mmol/m^2$, preferably 2 to 24 $mmol/m^2$.

Additionally, the heat-developable photosensitive image-recording material of the present invention optionally may include other materials known in the art for use in photothermographic image-recording material. These include, but are not limited to, antifoggants such as described in U.S. Pat. No. 4,743,533, antistatic materials, coating aids e.g, surfactants, activators and the like.

Also, the photosensitive elements optionally may contain additional layers commonly used in the art, such as spacer layers, a layer of an antihalation dye, and/or a layer of a filter dye arranged between differentially color-sensitive emulsion layers. A protective layer may also be present in the image-recording material of the present invention. The protective layer may contain a variety of additives commonly employed in the photographic art. Suitable additives include matting agents, colloidal silica, slip agents, organofluoro compounds, ultraviolet absorbers, accelerators, antioxidants, etc.

For forming color images in photographic image-recording systems, a color-providing compound according to an embodiment of the present invention can be used in both monochrome and full-color imaging systems such as disclosed in U.S. Pat. Nos. 4,098,783 and 3,719,489. Generally, a color-providing compound is associated with a light-sensitive silver halide emulsion which, after being exposed, is developed with an aqueous alkaline processing solution including a silver halide developing agent and a silver halide solvent. The imagewise distribution of silver ions such as contained in the soluble silver complex made available during processing of the emulsion migrates to the associated color-providing material which undergoes cleavage in the presence of the complex to release an imagewise distribution of the more diffusible reagent, e.g., color-providing group. The subsequent formation of a color image is the result of the differential in diffusibility between the color-providing compound and the liberated color-providing group whereby the imagewise distribution of the more diffusible color-providing group released in undeveloped and partially developed areas is free to transfer to the image-receiving layer. The color photographic image-recording materials using the compounds of this invention can be prepared in accordance with such procedures as described in U.S. Pat. Nos. 4,098,783 and 3,719,489, the disclosures of both being herein incorporated by reference.

The heat-developable photosensitive image-recording material according to the present invention can be used to form monochrome or multicolor images. If the image-recording material is to be used to generate a full-color image, it generally has three different heat-developable light-sensitive layers each releasing a different color dye as a result of thermal development.

Where multicolor images are desired, one or more layers containing a scavenger for silver ion and/or soluble silver complex may be employed between the photosensitive emulsion layers to enhance color separation. By virtue of the silver scavenger layer(s) being positioned between the emulsion layers, the migration of the imagewise distribution of soluble silver ions or soluble silver complex formed during processing of each emulsion layer is confined to the area of the compound associated with each emulsion layer and prevented from diffusing into the area of the compound associated with the other emulsion layer or layers. Silver scavengers which may be employed in the present invention include those described in U.S. Pat. No. 4,060,417.

The color-providing compounds of an embodiment of the present invention may be used in a system which utilizes dye developers, as well as, other image dye-releasing compounds, as described in U.S. Pat. No. 4,740,448. The color photothermographic image-recording materials using the compounds of this invention can be prepared in accordance with such procedures as disclosed in Research Disclosure No. 17029. The thermographic image recording materials using the compounds of this invention can be prepared as described in U.S. Pat. Nos. 5,328,799 and 5,436,108.

The compound of the invention may be added in the same layer as the photosensitive silver halide/silver salt oxidizer emulsion layer or in a layer on either side of the photosensitive emulsion layer. However, it is generally preferred that the color-providing compound be placed so that exposure does not occur through the dye. If exposure is made through the dye, the dye may absorb the light needed to expose the silver halide. In certain instances, it may be desirable to separate the compound from the emulsion layer by a spacer layer. Where the particular compound chosen tends to be migratory during storage and/or thermal development of the heat-developable photosensitive system, it is preferred that the compound be in a separate layer and more preferably, that it be in a layer furthest from the image-receiving layer. The amount of compound used varies with the type chosen but generally an mount of 0.25 to 2.0 $mmol/m^2$ is used.

The compound of the invention may be incorporated into the photographic layer(s) of the heat-developable photosensitive system by any suitable method. For example, the compounds can be dissolved in a low boiling and/or high boiling solvent and dispersed in the binder, they can be dispersed in aqueous solutions of suitable polymers, e.g., gelatin, by means of a ball mill, or they can be solvent coated using any organic solvent that will also dissolve gelatin, e.g., trifluoroethanol or dimethylsulfoxide.

The heat-developable photosensitive diffusion transfer materials of the present invention include those wherein the photosensitive silver halide emulsion layer(s) and the image-receiving layer are initially contained in separate elements which are brought into superposition subsequent or prior to exposure. After development the two layers may be retained together in a single element, i.e., an integral negative-positive film unit or they can be peeled apart from one another.

Alternatively, rather than being in separate elements, the photosensitive layer(s) and the image-receiving layer may initially be in a single element wherein the negative and positive components are contained in a heat-developable photosensitive laminate or otherwise retained together in an integral structure. After heat-development, the two layers may be retained together as a single element or they can be peeled apart from one another. Where the photosensitive silver halide emulsion layer(s) and the image-receiving layer are retained together as an integral negative-positive film unit, a masking layer, e.g., titanium dioxide, is necessary to conceal the untransferred dye from the final image.

Where the photothermographic image-recording material of the invention comprises separate elements which are brought together prior, or subsequent, to exposure, it is preferred that the compound be located in a layer which underlies the silver halide emulsion layer which in turn underlies the organic silver salt layer. In this embodiment, it is preferred to expose the photosensitive layer through the outermost layer, so that the exposure is not made through the compound, prior to superimposing the two separate elements in order to carry out the remaining steps of the photothermographic processing. Similarly, where all of the layers of the heat-developable, image-recording material are carded by one support, it is preferred to arrange the image-receiving layer adjacent to the support and underlying, in succession, the compound, the silver halide emulsion layer and the organic silver salt layer. Exposure is preferably made through the outermost layer.

The photosensitive image-recording material of the present invention may be exposed by any of the methods used in the photographic art, e.g., a tungsten lamp, a mercury vapor lamp, a halogen lamp, fluorescent light, a xenon flash lamp or a light emitting diode including those which emit infrared radiation.

The photosensitive image-recording material of the present invention is heat-developed after imagewise exposure. This is generally accomplished by heating the material at a temperature in the range of from about 80° to 200° C., preferably in the range of from about 100° to 150° C., for a period of from about 1 to 720 seconds, preferably from about 1.5 to 360 seconds. Heat may be used alone or heat may be applied simultaneously with pressure, if necessary, to create good thermal contact between the photosensitive and image-receiving elements. Pressure can be applied simultaneously with the heat required for thermal development by using heated rollers or heated plates. Alternatively, heat and, if required, pressure can be applied subsequent to thermal development in order to transfer the released reagent.

Any method of heating that can be employed in heat-developable photosensitive systems may be applied to the heat-developable image-recording material of the present invention. Thus, for example, heating may be accomplished by using a hot plate, an iron, heated rollers or a hot drum.

The image-recording materials of the present invention are useful in photographic imaging systems, such as diffusion transfer, utilizing silver halide wherein the method of processing employs wet processing, e.g., contacting an exposed silver halide emulsion with an aqueous processing composition. Hence, the image-recording material for use in diffusion transfer color process, in this context, further comprises means for applying a photographic processing composition comprising an aqueous alkaline solution of silver halide developing agent and a silver halide solvent.

In addition, thermographic and photothermographic processed photographic systems may be processed in the presence of a base or a base-precursor. It is known in the art that the base or base-precursor may be either added to the system or generated internally by reactions of compounds incorporated in photographic systems. It is also known in the art that thermographic and photothermographic processed photographic systems may be processed in the absence of a base or a base-precursor, for example, the color-providing moiety transfers due to the hydrophobicity of the polymer such as polyvinylchloride which is coated on the image-receiving support to receive the color-providing moiety.

In an embodiment of the image forming system of the present invention, water is used as a reaction medium. Water may be available by any suitable means, for example, by supplying water from without the system, or by previously incorporating water-containing capsules or similar means in the system and breaking the capsules by heating or the like to release the water.

The invention will now be described further in detail with respect to specific preferred embodiments by way of examples, it being understood that these are intended to be illustrative only, and the invention is not limited to the materials, procedures, amounts, etc. recited therein. All parts and percentages recited are by weight unless otherwise stated.

EXAMPLES

In the following examples, the silver iodobromide dispersion is a 0.2 μm cubic unsensitized iodobromide (2% iodide) emulsion prepared by standard techniques known in the art. The silver salt oxidizer, thermal solvent, color-providing material and reducing agents used in the examples were added to the coating compositions as dispersions. The various dispersions were prepared by the specific procedures described below or by analogous procedures but using different reagents as noted. The other components of the layers, e.g., succinaldehyde, benzotriazole and glyoxal when added were added to the coating compositions as aqueous solutions.

(1) Silver Salt Dispersion

Benzotriazole (415 g) was added to 325 ml of concentrated ammonium hydroxide. To the resulting solution was added 450 g of gelatin and the mixture was diluted to a total volume of 6 liters with water. To this mixture, in the dark and at 40° C., was added with stirring, over a one-hour period, a mixture prepared by combining 550 g of silver nitrate with 500 ml of concentrated ammonium hydroxide and diluted to a total of 2.1 liters with water. The mixture stood at room temperature (RT) for about 60 minutes and then the material was washed using standard emulsion washing procedures and the pH adjusted to 6 and the pAg adjusted to 7.4.

(2) Thermal Solvent Dispersion

The thermal solvent was dispersed in a mixture of 10% aqueous polyvinylpyrrolidone, 5% aqueous Alkanol XC (available from duPont, Wilmington, Del.) and water. The resulting mixture was ground in a ball mill for 7 hours. Water was introduced for washing purposes during the isolation of the dispersion.

(3) Dispersion of Color-Providing Compounds 1.6 g of dye-providing material, the compound of formulas (i), (ii) or (iii) were dissolved in 5.0 g of ethyl acetate. 0.8 g of tricresylphosphate was added and the mixture was stirred and heated to 42° C. To the mixture at 40° C. was added a solution containing 21 g water, 4 g of 5% aqueous Alkanol XC and 8.5 g of 17.5% aqueous gelatin. The mixture was sonified with an ultrasonic probe for one minute in order to form a dispersion. The dispersion was stirred at 60° C. for 20 minutes to remove the ethyl acetate, followed by the addition of 14.1 g water.

(4) Reducing Agent Dispersion

Exactly 3.0 g of 4-hydroxymethyl4-methyl-1-phenyl-3-pyrazolidone (Dimezone S) was added to 4.0 g of water and 3.0 g of 5% aqueous Alkanol XC. The resulting mixture was ground in a ball mill for 16 hours. The resulting dispersion was diluted with water during isolation.

EXAMPLE I

Preparation of Compound (i)

2.6 g (0.03624 mol; 2.36 ml) acetylchloride and 10 g (30.2 mmol) n-octadecylbenzene in 50 ml methylenechloride were added sequentially to a solution of 4.85 g (0.03624 mol) aluminumchloride in 50 ml methylenechloride, at RT. After stirring for two hours, the solution was quenched by the addition of an ice cold solution of 10% HCl and the organic phase was separated. The aqueous phase was extracted with methylenechloride. The combined organic phases were dried over $MgSO_4$, and concentrated to yield 10.1 g (89.6%) of product. The reaction was carried out with a slight modification of the process described by C. G. Overberger, C. Frazier, J. Mandelman, H. F. Smith, J. Am. Chem. Soc. 75, 3326 (1953). The structure of 4-octadecyl-acetophenone was confirmed by NMR and mass spectroscopy.

The general method described by C. Djerassi, M. Gorman, F. X. Markley, E. B. Oldenburg, J. Am. Chem. Soc. 77, 568 (1955), was performed. Specifically, 4.826 g (0.0302 mol; 1.65 ml) bromine was added dropwise at 0° C. to a solution of 10.1 g (0.0271 mol) 4-octadecyl-acetophenone and a catalytic amount of aluminumchloride in 100 ml of ethyl ether. When the addition was completed, the reaction mixture was allowed to warm up to RT and, then concentrated to yield 12.1 g (99.1%) of white solids with a melting point (Mp) of 67°–70° C. The structure of 4-octadecyl-bromoacetophenone was confirmed by NMR and mass spectroscopy.

The aforementioned general method described by C. Djerassi was performed. Specifically, a solution of 12.1 g (0.027 mol) 4-octadecyl-bromoacetophenone in 100 ml acetone was added to 4.38 g (0.03 mol) potassium ethylxanthogenate and 100 ml acetone between 5°–10° C. and stirred for two hours. The reaction mixture was concentrated and the resulting 12.8 g (96.9%) of white solids (Mp 63°–65° C.) were washed with water. The structure of S-(4-octadecyl-benzoyl)-methyl-O-ethylxanthogenate was confirmed by NMR and mass spectroscopy.

The aforementioned general method described by C. Djerassi was performed. Specifically, a solution of 12.8 g (0.027 mol) S-(4-octadecyl-benzoyl)-methyl-O-ethylxanthogenate in 300 ml ether was added dropwise at RT without cooling to 1.43 g (0.038 mol) lithium aluminum hydride suspended in 25 ml ether. After the solution refluxed for two hours, it was quenched with approximately 200 ml ice/water and, 10% HCl was added until the reaction mixture cleared up. The organic and aqueous phases were separated and, the aqueous phase was extracted with ether. The combined organic phases were dried over $MgSO_4$ and concentrated to 10.3 g (95.3%) of waxy solids. The structure of α-hydroxy-β-mercapto-4-octadecyl-ethylbenzene was confirmed by NMR spectroscopy.

This reaction was carded out according to the general "Vilsmeier formylation" conditions, as described for example in Houben-Weil: Methoden der Organischen Chemie VII/1 29, (Georg Thieme Verlag 1954, Stuttgart). Specifically, 19.92 g (12 ml, 0.124 mol) phosphorous oxychloride was added over a period of 30 minutes at 0° C. to a solution of 20 g (0.124 mol) N-methyl-N-cyanomethyl-aniline in 35 ml DMF. The reaction mixture was allowed to attain RT and, then stirred at 100° C. for three hours. The solution was poured into 250 ml ice/water, adjusted to pH 8 and, then extracted with 3×50 ml methylenechloride. The combined organic layers were dried over $MgSO_4$ and, then concentrated on a rotary evaporator, resulting in 23 g of red oil (98%). The structure of N-methyl-N-cyanoethyl-4-aminobenzaldehyde was confirmed by NMR spectroscopy.

15 g (0.079 mol) N-methyl-N-cyanoethyl-4-aminobenzaldehyde was suspended in a solution of 7 g (0.175 mol) sodium hydroxide in 40 ml water; refluxed until a homogenous solution was obtained; cooled to 0° C.; neutralized with a 15% HCl solution; and extracted with 4×50 ml ethylacetate. The combined organic phases were dried over MgSO4 and concentrated to 14.2 g (86.5%) oil, which solidified upon standing. The structure of N-methyl-N-carboxyethyl-4-amino-benzaldehyde was confirmed by NMR and mass spectroscopy.

This reaction used "Mukaiyama conditions," a general method described by T. Mukaiyama, M. Usui, E. Shimada, Chemistry Letters 1045 (1975). Specifically, 1 g (4.825 mmol) (N-methyl-N-2-carboxyethyl)-4-aminobenzaldehyde, 1.46 g (4.825 mmol) 4-hydroxy-4'-dimethylamino azobenzene and 0.97 g (9.65 mmol; 1.34 ml) triethylamine were added to a suspension of 1.48 g (4.825 mmol) N-methyl-2-chloro-pyridinium iodide in 20 ml methylenechloride. After two hours, 0.7 g N-methyl-2-chloro-pyridinium iodide was added. The reaction mixture was refluxed for three hours and, then filtered to remove the solids. The mother liquor was concentrated. The crude aldehyde dye was recrystallized from acetonitrile to yield 1.8 g (86.5%) of pure aldehyde dye. The structure of the aldehyde dye (Compound A), $C_{25}H_{26}N_4O_3$, was confirmed by NMR and mass spectroscopy.

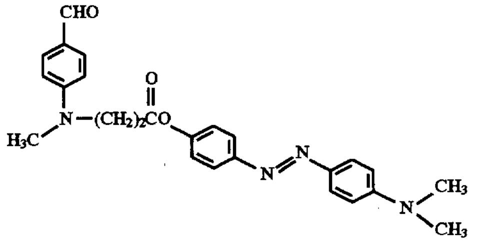

(A)

This reaction used a modification of the procedure described by T. H. Fife and R. Natarajan, J. Am. Chem. Soc. 108, 2425 (1986). Specifically, 4.31 g (0.01 mol) aforementioned aldehyde dye, $C_{25}H_{26}N_4O_3$, 4.06 (0.001 mol) α-hydroxy-β-mercapto- 4-octadecyl-ethylbenzene and a catalytic amount of $BF_3$ were refluxed for four hours in 100 ml benzene, during which the water was separated by a Dean-Stark trap. The reaction mixture was concentrated. 3.2 g (37.2% yield) pure product resulted from purification on a silica gel column using ether as an eluent. The structure of compound (i), $C_{51}H_{70}N_4O_3S$, was confirmed by NMR and mass spectroscopy.

EXAMPLE II

A heat-developable photosensitive material was prepared using compound (i) wherein the photosensitive material comprised a gelatin subcoated 4 mil polyester film base (available from DuPont) having coated thereon in succession the following layers:

Layer 1

| | |
|---|---|
| Gelatin (Inert, deionized, derivatized bone gelatin, available from Rousselot, France) | 409 mg/m$^2$ |
| m-toluamide | 495 mg/m$^2$ |
| Dye-providing material (Compound (i)) | 0.845 mmol/m$^2$ |
| Glyoxal | 14 mg/m$^2$ |

Layer 2

| | |
|---|---|
| Gelatin | 678 mg/m$^2$ |
| m-toluamide | 495 mg/m$^2$ |
| Dimezone S | 7.95 mmol/m$^2$ |
| Glyoxal | 14 mg/m$^2$ |
| Silver bromide (0.2 micron unsensitized silver bromide emulsion) | 2.009 mmol/m$^2$ |

Layer 3

| | |
|---|---|
| Gelatin | 678 mg/m$^2$ |
| m-toluamide | 495 mg/m$^2$ |
| Glyoxal | 14 mg/m$^2$ |
| Silver benzotriazole | 1.238 mmol/m$^2$ |

Receiver materials were prepared comprising baryta paper coated with an image-receiving layer of polyvinyl chloride coated at a coverage of (12 g/m$^2$). The receiver materials further included, coated over the polyvinylchloride layer, a layer comprising:

| | |
|---|---|
| Gelatin | 678 mg/m$^2$ |
| N-methylnicotinamide | 1636 mg/m$^2$ |
| Triethanolamine | 2152 mg/m$^2$ |
| Hydroxy PMT (1-(4-hydroxyphenyl)-1H-tetrazole-5-thiol) | 452 mg/m$^2$ |

The assembly was processed for 90 seconds at 120° C. at a pressure of 26 psi using a heated plate. An image was only obtainable at these processing conditions when a slight amount of water was sprayed onto the negative.

The maximum reflection density ($D_{max}$) and the minimum density ($D_{min}$) of the resulting image were measured using a reflection densitometer (MacBeth, model RD 514). The heat-developable photosensitive material gave $D_{max}$=0.61 and $D_{min}$=0.36.

EXAMPLE III

Preparation of Compound (ii)

The method of preparation of compound (ii) is the preparation described in example I and, then two additional steps using "Mukaiyama conditions," as described above. 2.2 g (10.62 mmol) N-methyl-N-2-carboxyethyl-4-aminobenzaldehyde, 3 g (5.31 mmol) dihydroxy coupler dye (Compound B)

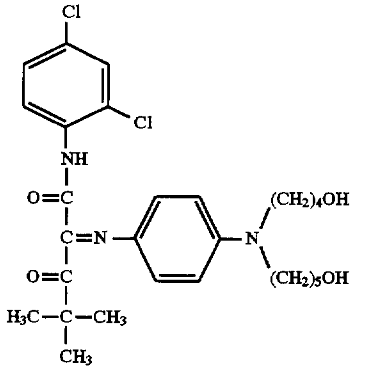

(B)

(the preparation of (B) is described in U.S. Pat. No. 5,340, 689) and 2.14 g (21.16 mmol) triethylamine were added to a suspension of 3.36 g (12.75 mmol) N-methyl-2-chloropyridinium iodide in 20 ml methylenechloride. The reaction mixture was refluxed for 18 hours and filtered to remove the solids. The mother liquor was concentrated. 2.0 g (20.4%) of pure product resulted from purification on a silica gel column using THF as an eluent. The structure was confirmed by NMR and mass spectroscopy.

This reaction used a modification of the aforementioned procedure described by T. H. Fife. 2 g (2.12 mmol) dialdehyde coupler dye (Compound C)

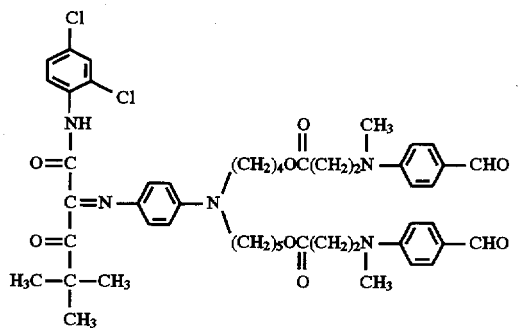

(C)

1.75 g (4.25 mmol) α-hydroxy-β-mercapto-4-octadecyl-ethylbenzene, and a drop of 10% $BF_3$ solution in propanol were refluxed in 75 ml benzene for 24 hours, whereupon the addition of the above amount of α-hydroxy-β-mercapto-4-octadecyl-ethylbenzene was repeated and the reflux continued for 24 hours. The reaction mixture was concentrated and purified on a silica-gel/ether column. 3.52 g (96.4% yield) of pure product was recovered. The structure of compound (ii), $C_{102}H_{147}Cl_2N_5O_8S_2$, was confirmed by NMR and mass spectroscopy.

EXAMPLE IV

A heat-developable photosensitive material was prepared using compound (ii) wherein the photosensitive material comprised a gelatin subcoated 4 mil polyester film base (available from DuPont) having coated thereon in succession the following layers:

Layer 1

| | |
|---|---|
| Polyvinylalcohol (Airval #540) | 818 mg/m$^2$ |
| m-toluamide | 1560 mg/m$^2$ |
| Dye-providing material (Compound (ii)) | 0.742 mmol/m$^2$ |

Layer 2

| | |
|---|---|
| Gelatin | 689 mg/$m^2$ |
| m-toluamide | 1560 mg/$m^2$ |
| Dimezone S | 3.87 mmol/$m^2$ |
| Silver bromide | 2.01 mmol/$m^2$ |

Layer 3

| | |
|---|---|
| Polyvinylalcohol (Airval #205) | 818 mg/$m^2$ |
| m-toluamide | 1560 mg/$m^2$ |
| Silver benzotriazole | 0.915 mmol/$m^2$ |

Receiver materials were prepared comprising baryta paper coated with an image-receiving layer of polyvinyl chloride coated at a coverage of (12 g/$m^2$). The receiver materials further included, coated over the polyvinylchloride layer, a layer comprising:

| | |
|---|---|
| Gelatin | 678 mg/$m^2$ |
| N-methylnicotinamide | 1636 mg/$m^2$ |
| Triethanolamine | 2152 mg/$m^2$ |
| Hydroxy PMT (1-(4-hydroxyphenyl)-1H-tetrazole-5-thiol) | 452 mg/$m^2$ |

The heat-developable photosensitive material was exposed to white light for $10^{-2}$ seconds, using an EGG sensitometer Mark IV unit. An exposure time of $10^{-2}$ seconds was repeated at three separate intervals. The assembly was processed for 180 seconds at 120° C. at a pressure of 26 psi using a heated plate.

The heat-developable photosensitive material gave $D_{max}$= 0.88 and $D_{min}$=0.47.

EXAMPLE V

Compound (iii) was prepared by the following method: 0.3 g (0.3 mmol) of Compound D, $C_{43}H_{38}N_{10}O_{14}S_3$, (D)

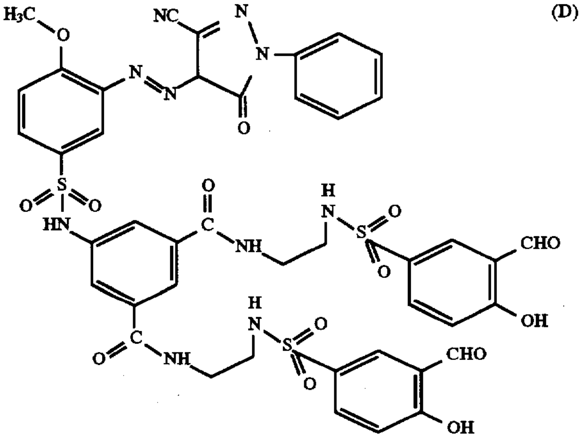

and 0.24 g (0.6 mmol) α-hydroxy-β-mercapto-4-octadecylethylbenzene were refluxed in 20 ml THF for 12 hours. The reaction mixture was concentrated and chromatographed on a silica gel column using ether, ethyl ether, and THF, e.g., 1:1:1 solution as eluent. 0.50 g pure product was recovered. The structure of compound (iii) was confirmed by NMR and mass spectroscopy.

The following compounds were also used in this example:

(E)

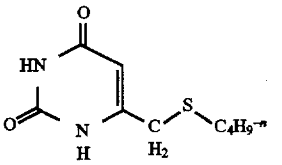

(F)

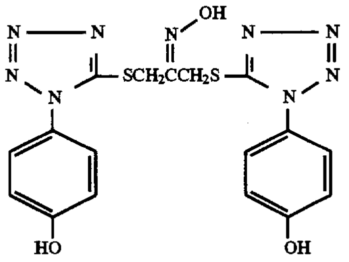

A heat-developable photosensitive material was prepared wherein the photosensitive material comprised a gelatin subcoated 4 mil polyester film base (available from Dupont) having coated thereon in succession the following layers:

Layer 1

| | |
|---|---|
| Gelatin | 807 mg/$m^2$ |
| Dye-providing material (Compound (iii)) | 0.6003 mmol/$m^2$ |
| Compound E (6-Butylthiomethyluracil) | 5.021 mmol/$m^2$ |

Layer 2

| | |
|---|---|
| Gelatin | 807 mg/$m^2$ |
| Silver bromide (0.25 micron unsensitized silver bromide emulsion) | 3.21 mmol/$m^2$ |
| Graphidone (4-Methyl-phenidone) | 645.6 mg/$m^2$ |
| Compound F | 107.6 mg/$m^2$ |

Layer 3

| | |
|---|---|
| Gelatin | 699.46 mg/$m^2$ |
| Zinc hydroxide | 14.073 mmol/$m^2$ |

Layer 4

| | |
|---|---|
| Succinaldehyde | 129 mg/$m^2$ |

The receiver materials were coated over the white polyester base (ICI 6110), having coated thereon in succession the following layers:

Layer 1

| | |
|---|---|
| Graft copolymer (4-vinyl pyridine and vinyl benzyl trimethylammonium chloride grafted onto hydroxyethylcellulose) | 3228 mg/$m^2$ |
| Diepoxy | 53.8 mg/$m^2$ |

Layer 2

| | |
|---|---|
| Gum arabic | 807 mg/m$^2$ |

Layer 3

| | |
|---|---|
| Guanidine picolinate | 5111 mg/m$^2$ |

The negative was dipped in water, laminated with the positive sheet, and heated for 60 seconds at 90° C. The heat-developable photosensitive material gave $D_{max}$=0.33 and $D_{min}$=0.17.

Examples II and IV were processed base-free, i.e., they did not contain any added base or base-precursor and, water-free, i.e., no water was added to aid in development or transfer. It is recognized that while certain of the auxiliary ligands used in the examples may be classified as weak bases, such ligands would not be considered to be bases or base-precursors as those terms are used in Japanese Kokai No. 59-180548. However, as stated earlier, the compounds of the present invention may be used in heat-developable imaging materials containing a base or base-precursor such as disclosed in U.S. Pat. No. 3,260,598.

Since certain changes may be made in the above subject matter without departing from the spirit and scope of the invention herein involved, it is intended that all matter contained in the above description and the accompanying examples be interpreted as illustrative and not in any limiting sense.

What is claimed is:

1. A compound represented by the formula

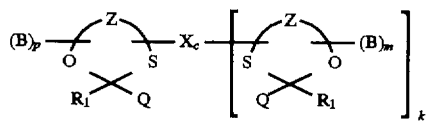

wherein:

$R_1$ is represented by any of the formulae below (IIa)

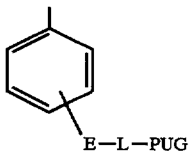

(IIb)

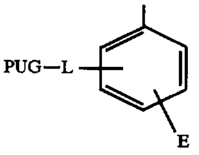

(IIc)

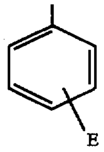

E is an electron donating group selected from the group consisting of amino, substituted amino selected from the group consisting of

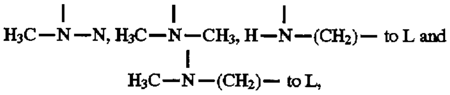

alkoxy, hydroxyl, alkyl and thioalkyl, provided that when $R_1$ is represented by formula II(a), E is selected from the group consisting of amino, substituted amino selected from the group consisting of

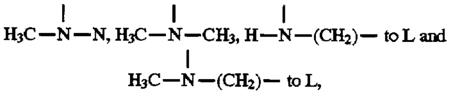

alkoxy, alkyl and thioalkyl; L represents a divalent organic linking group containing at least one carbon atom; PUG represents a photographically useful group selected from the group consisting of a dye radical and a dye intermediate;

Q represents a hydrogen atom, alkyl, benzene, dimethylaminobenzene, alkoxy, or thioalkyl, or Q is the same as $R_1$ when $R_1$ is represented by formula (IIa) or formula (IIb), or Q is formula (IIa) when $R_1$ is represented by formula (IIb), or Q is formula (IIb) when $R_1$ is represented by formula (IIa), or when $R_1$ is represented by formula (IIc), Q is -L-PUG-, provided that at least one of $R_1$ and Q includes PUG;

Z represents the carbon atoms necessary to complete a 5- or 6-membered 1,3-sulfur-oxygen ring system;

B represents a ballast group for rendering said compound substantially immobile and non-diffusible during processing selected from the group consisting of an alkyl chain having from 10 to 22 carbon atoms and a phenyl ring substituted with an alkyl group having from 8 to 22 carbon atoms;

p is an integer from 0 to 3;

c is 0 or 1;

m is an integer from 0 to 3;

k is 0 when c is 0; k is 1, 2, or 3 when c is 1; and

X represents a multivalent chemical linkage which may attach one, two or three additional said 1,3-sulfur-oxygen ring systems to said 1,3-sulfur-oxygen ring system, when k is 1, 2 or 3, respectively.

2. A compound according to claim 1 wherein Z represents the carbon atoms necessary to complete a 5-membered 1,3-sulfur-oxygen ring system.

3. A compound according to claim 1 wherein B is a phenyl ring substituted with an alkyl group having from 8 to 22 carbon atoms.

4. A compound according to claim 1 wherein c is 1.

5. A compound according to claim 1 wherein c is 0.

6. A compound according to claim 2 wherein k and c are 1, represented by the formula

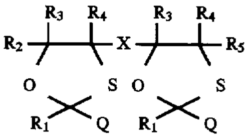

wherein:

$R_2$, $R_3$, $R_4$, and $R_5$ are each independently hydrogen, phenyl, alkyl, or a ballast group for rendering said compound substantially immobile and non-diffusible during processing.

7. A compound according to claim 5 wherein said compound is represented by the formula

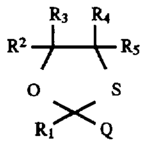

wherein:

$R_2$, $R_3$, $R_4$, and $R_5$ are each independently hydrogen, phenyl, alkyl, or a ballast group for rendering said compound substantially immobile and non-diffusible during processing.

8. A compound according to claim 2 wherein c is 0, p is 1, said PUG is a dye radical, $R_1$ is represented by said formula (IIa), and B is a phenyl ring substituted with an alkyl group having from 8 to 22 carbon atoms.

9. A compound according to claim 1 wherein Z represents the carbon atoms necessary to complete a 6-membered 1,3-sulfur-oxygen ring system.

10. A compound according to claim 1 wherein B is an alkyl chain having from 10 to 22 carbon atoms.

11. A compound according to claim 1, wherein E is selected from the group consisting of 12. A compound according to claim 1 wherein $R_1$ is represented by said formula II(a).

13. A compound according to claim 1 wherein Q is selected from the group consisting of a hydrogen atom and -L-PUG.

14. A compound according to claim 1 wherein c, k, m and p are 1.

15. A compound according to claim 1 wherein E is selected from the group consisting of $H_3C—N—H$, $H_3C—N—CH_3$, $H—N—(CH_2)—$ to L, $H_3C—N—(CH_2)—$ to L $O—H$, $O—CH_3$ and $O—CH_2—$ to L.

16. A compound according to claim 2 wherein c is 0, p is 1, said PUG is a dye radical and B is an alkyl chain having from 1 to 22 carbon atoms.

17. A compound according to claim 6 wherein said ballast group is selected from the group consisting of an alkyl chain having from 10 to 22 carbon atoms and a phenyl ring substituted with an alkyl group having from 8 to 22 carbon atoms.

18. A compound according to claim 7 wherein said ballast group is selected from the group consisting of an alkyl chain having from 10 to 22 carbon atoms and a phenyl ring substituted with an alkyl group having from 8 to 22 carbon atoms.

19. A compound according to claim 8 wherein E is selected from the group consisting of $O—CH_2—$ to L, $H—N—(CH_2)—$ to L and $H_3C—N—(CH_2)—$ to L.

20. A compound according to claim 19 wherein said PUG is a dye radical and B is a phenyl ring substituted with an alkyl group having from 8 to 22 carbon atoms.

* * * * *